United States Patent
Shenker

(10) Patent No.: US 11,357,653 B2
(45) Date of Patent: Jun. 14, 2022

(54) DORSIFLEXION ASSIST DEVICE

(71) Applicant: Evgeny Shenker, New York, NY (US)

(72) Inventor: Evgeny Shenker, New York, NY (US)

(*) Notice: Subject to any disclaimer, the term of this patent is extended or adjusted under 35 U.S.C. 154(b) by 150 days.

(21) Appl. No.: 15/931,477

(22) Filed: May 13, 2020

(65) Prior Publication Data

US 2021/0353447 A1    Nov. 18, 2021

(51) Int. Cl.
| | | |
|---|---|---|
| *A61F 5/01* | (2006.01) |
| *A63B 21/00* | (2006.01) |
| *A63B 21/02* | (2006.01) |
| *A63B 21/065* | (2006.01) |
| *A63B 23/08* | (2006.01) |

(52) U.S. Cl.
CPC ............ *A61F 5/0113* (2013.01); *A63B 21/00* (2013.01); *A63B 21/02* (2013.01); *A63B 21/065* (2013.01); *A63B 23/08* (2013.01)

(58) Field of Classification Search
CPC .. A61F 5/00; A61F 5/01; A61F 5/0111; A61F 5/0113; A61F 5/0104; A61F 5/019; A61F 5/127; A61F 5/37; A61F 5/058; A61F 5/0585; A61F 5/0102; A61F 2005/0165; A61F 2005/0167; A61F 2005/0179; A61F 2005/0169; A61F 13/06; A61F 13/061; A61F 13/063; A61F 13/064; A61F 13/066; A61F 5/14; A43B 7/20; A43B 7/14; A41D 13/05; A41D 13/0543; A41D 13/06; A61H 3/00; A61H 3/007; A61H 1/02; A61H 1/0237; A61H 1/0266; A63B 21/0557; A63B 21/04; A63B 21/0407; A63B 21/0421; A63B 21/0442; A63B 21/4011; A63B 21/4012; A63B 21/4013; A63B 21/4014; A63B 21/4015; A63B 21/08; A63B 21/081; A63B 21/082; A63B 21/083; A63B 21/084; A63B 21/085
USPC ............... 602/27, 28, 23, 16, 5, 20; 128/882
See application file for complete search history.

(56) References Cited

U.S. PATENT DOCUMENTS

2010/0304937 A1* 12/2010 Spencer ............. A63B 21/4015
                                                                482/79
2021/0052931 A1*  2/2021 Louis ..................... A63B 21/02

* cited by examiner

*Primary Examiner* — Erin Deery
*Assistant Examiner* — Daniel A Miller
(74) *Attorney, Agent, or Firm* — Michael J. Feigin, Esq.; Feigin and Fridman LLC

(57) ABSTRACT

A dorsiflexion (or eversion) assistance device attaches around an ankle and foot, such us over footwear. A tensioned cord is extended between a portion attached to the ankle and a portion attached to the foot. This tensioned cord is attached to one of a plurality of portals of a connector attached to the ankle and connector attached to the superior side of the foot depending on a need for greater assistance on a left, medial, or right side. The connector on the ankle can be a bearing movable or rotatable front/back, left/right and around so as to allow the tensioned cord to move as the wearer walks as well as angle the tensioned cord in a resting or walking state.

16 Claims, 12 Drawing Sheets

Setup-A represents "No Falange extension"
Setup-B represents "Connecting Falange extension Trigonometry Setup-A:
    $\tan(\theta) = $ Opposite / Adjacent

Q1= 28.6 °

Setup-B:
    $\tan(\theta) = $ Opposite / Adjacent

Q2= 59.74 °

DORSIFLEXION ASSIST DEVICE

FIELD OF THE DISCLOSED TECHNOLOGY

The disclosed technology relates generally to a dorsiflexion assistance, and more specifically to such a device with removable tension cords attachable at various parallel and non-parallel connecting portals.

BACKGROUND

Dorsiflexion uses the muscles in the front part (anterior) of the foot. People with a condition known as "drop foot" have difficulty walking because flexing their foot towards their ankle is impaired or not possible. Devices to help lift a foot are used to try and aid a person to walk in such a manner. There is a need in the art to help a person walk, but also allow and require use of the muscles. Otherwise, assist devices can cause the muscles used for dorsiflexion to become unused and atrophy making the problem worse in the long term rather than better.

SUMMARY OF THE DISCLOSED TECHNOLOGY

Dorsiflexion is the action of raising the foot upwards towards the shin. A device which assists with dorsiflexion is disclosed herein which is has, at least a portion which is wrapped around (connected to, by way of a member which surrounds) the ankle. This can be part of an article of footwear extending to the ankle, an anklet or band tensioned to the ankle, or otherwise. An anterior member of the device has a substantially vertically disposed portal (where, "vertical" is relative to a longest linear length of a lower leg, tibia, fibula, or the ground). This portal extends in a vertical direction with openings at each of a superior end and anterior end thereof. The directional indicators in this disclosure (e.g. "anterior", "superior") are relative to each other and/or a person wearing the device as intended. The portal has an interior which is wider in a lateral direction than the anterior disposed portal.

A slidable member is sized to fit across the lateral direction of the vertically disposed portal of the anterior member (sized to fit, in this instance, being defined as, "having a width wider than the anterior disposed portal and which fits, width-wise, such than it can be inserted and removed completely into the superior end of the portal). A connecting flange extends through the anterior portal of the substantially vertically disposed portal and is fixed to the slidable member. "Fixed" or "fixedly" is defined as, "of a unitary structure and/or designed to remain whole and unchanged relative to the part to which it is fixed through at least 100 uses thereof." A multi-portal connecting end (an end having more than one portal passing through itself) is connected to the connecting flange in a fixed or removable manner, such as by way of a bearing allowing movement in some or all of an anterior, posterior, lateral, and combined directions thereof.

A tensioned cord extends, in embodiments of the disclosed technology, from a portal of the multi-portal connecting end to a foot connector. The tensioned cord attaches at a dorsal side of the foot connector in some embodiments. The "tensioned cord" is a resilient length of material which can be bent, expanded in length, and contracted in length after expanded. "Resilient" is defined as "able to change shape and return substantially to an original shape after over 100 such changes." The multi-portal connecting end has at least three substantially identical portals in parallel to one another in some embodiments with the middle (central) portal thereof inline with the connecting flange and centered with respect to the anterior member. The foot connector can also have a plurality of portals in parallel to one another along an anterior side thereof. The tensioning cord, or multiple tensioning cords, can removably (designed for attachment and detachment at least 100 times) attach between/to any of the portals of the multi-portal connector and any of the portals of the foot connector. The portals used for connection are selected, in embodiments of the disclosed technology, based on the lateral location of each respective portal in order to assist dorsiflexion where a person is most weak with same (e.g. on a more left or right side/lateral or medial side). A weakest part is where dorsiflexion assist is needed most.

The slidable member and the connecting flange are movable only in a superior to anterior direction within the anterior member in some embodiments of the disclosed technology. The anterior member is adapted to be fixed relative to an ankle of a wearer thereof. The multi-portal connecting end is simultaneously anglably and rotationally connected to the connecting flange and held substantially in place relative to the anterior member when held taut, by way of a foot connector, to a dorsal side of a foot in some embodiments of the disclosed technology.

The foot connector extends around an article of footwear and dorsal muscles of a foot in embodiments of the disclosed technology. The foot has a plurality of first portals in parallel to each other and at least one additional portal which is more inferior and lateral in directional position relative to the first portals in some embodiments of the disclosed technology. Two or more tensioned cords can be used simultaneously to connect the ankle-wrapped section of the assist device with a foot-wrapped section of the assist device. For example, a first tensioned cord extends between a first portal of the multi-portal connecting end and one portal of the plurality of first portals of the foot connector. The first tensioned cord extends as described simultaneous to a second tensioned cord extending between a second portal of the multi-portal connecting end which is in parallel with the first portal thereof, and one of the additional portals of the foot connector which is more inferior and lateral in directional position to the first portals.

A method of using the dorsiflexion assist device described above can be carried out by way of any of the following steps, alone, in combination, and in any order such as the order provided below. An ankle connector is secured in a fixed position around an ankle. A foot connector is secured in a fixed position around an anterior and dorsal end of a foot. An anterior connector of the ankle connector is secured to an anterior side of the ankle. A slidable member is slid through a superior end of a portal of the anterior connector causing a connecting flange to extend through an anterior portal of the ankle connector. A first end of a first tensioned cord is attached (removably or fixedly) to a portal of a multi-portal connector. In such an instance, the multi-portal connector is rotatably held to the slidable member. A second end of the first tensioning cord is attached a portal fixed to the foot connector.

The connections of the tensioned cords to the ankle connector and dorsal side of the foot connector can be based on a selection of a distance from a medial center of the ankle connector to assist with dorsiflexion and/or eversion. Eversion is defined as, "the movement of the sole of the foot away from the median plane." A second tensioned cord connected between the ankle and foot connector can also be connected as such, such as to an as yet unused portal of each.

The portal to which the second tensioned cord can be connected can be more inferior and lateral (rather than medial, relative to the wearer) compared to the portal connected to said first tensioned cord.

Any device or step to a method described in this disclosure can comprise or consist of that which it is a part of, or the parts which make up the device or step. The term "and/or" is inclusive of the items which it joins linguistically and each item by itself.

DETAILED DESCRIPTION OF EMBODIMENTS OF THE DISCLOSED TECHNOLOGY

A dorsiflexion (or eversion) assistance device attaches around an ankle and foot, such us over footwear. A tensioned cord is extended between a portion attached to the ankle and a portion attached to the foot. This tensioned cord is attached to one of a plurality of portals of a connector attached to the ankle and connector attached to the superior side of the foot depending on a need for greater assistance on a left, medial, or right side. The connector on the ankle can be a bearing movable or rotatable front/back, left/right and around so as to allow the tensioned cord to move as the wearer walks as well as angle the tensioned cord in a resting or walking state.

Embodiments of the disclosed technology will become more clear in view of the following discussion of the figures.

Figure 1:
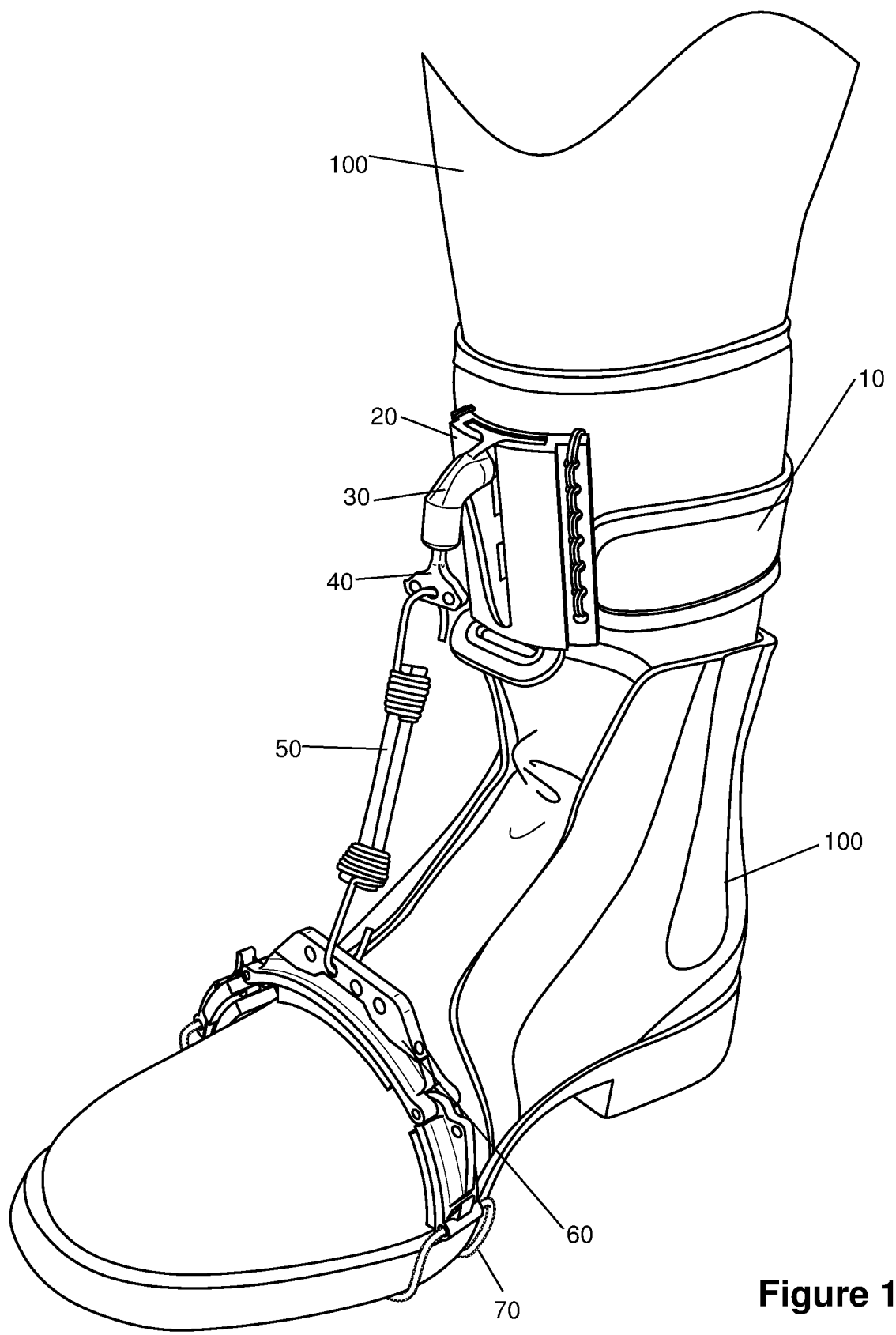
FIG. 1 shows a perspective view of a dorsiflexion assist device attached to a wearer in a resting position in an embodiment of the disclosed technology.

FIG. 1 shows a perspective view of a dorsiflexion assist device attached to a wearer in a resting position in an embodiment of the disclosed technology. An article of footwear 100 may be worn covering a foot and ankle of a person. Attached over the foot or ankle region of the footwear or otherwise around a foot an ankle of a person is a dorsiflexion assist device including an anterior member 20 with a substantially vertically disposed portal having an opening on the front (anterior) side and top (superior) side thereof. The anterior member 20 is held to and/or around an ankle of a wearer by a band 10. The anterior member 20 may additionally be held in place by being on top of the footwear 100 such that the footwear 100 prevents the anterior member 20 from falling lower. A slidable member 30 is placed within the portal of the anterior member with a portion fitting laterally therein such that the slidable member 30 can be lowered into the anterior member 20. Given that the anterior member 20 has a front-facing portal, a connecting flange 30 which forms a unitary piece with, or is otherwise connected to, the slidable member 20 extends out from the anterior portal of the anterior member 20.

A multi-portal connecting end 40 is connected into the connecting flange 30 in embodiments of the disclosed technology. The multi-portal connecting end 40 has a plurality of portals passing there-through and is connected to the connecting flange 30 in a manner which allows rotation with respect thereto. A bearing member (spherical region connected to a post) can be used to effectuate this connection such that the end of portals of the connecting end 40 can move, with respect of the connecting flange 30, in an anterior/posterior direction, lateral direction, and combination of such directions of movement.

A tensioned cord 50 connects between one of the portals of the multi-portal connecting end 40 and a portal of a foot connector 60. The foot connector 60 wraps around a foot or otherwise has portals on a top (superior) side of a foot. In this manner, the tension cord 50 extending between the anterior side of the ankle and superior side of the foot pulls (applies of force between) the anterior side of the ankle and superior side of the foot towards each other. The tensioned cord can have a first resting length and a second stretched length which is longer than it's length at rest. When attached between the portals of the connecting end 40 and foot connector 60, it can be stretched into the second stretched length such that force will be applied between the connectors as the tensioned cord pulls back towards its resting length.

Figure 2:
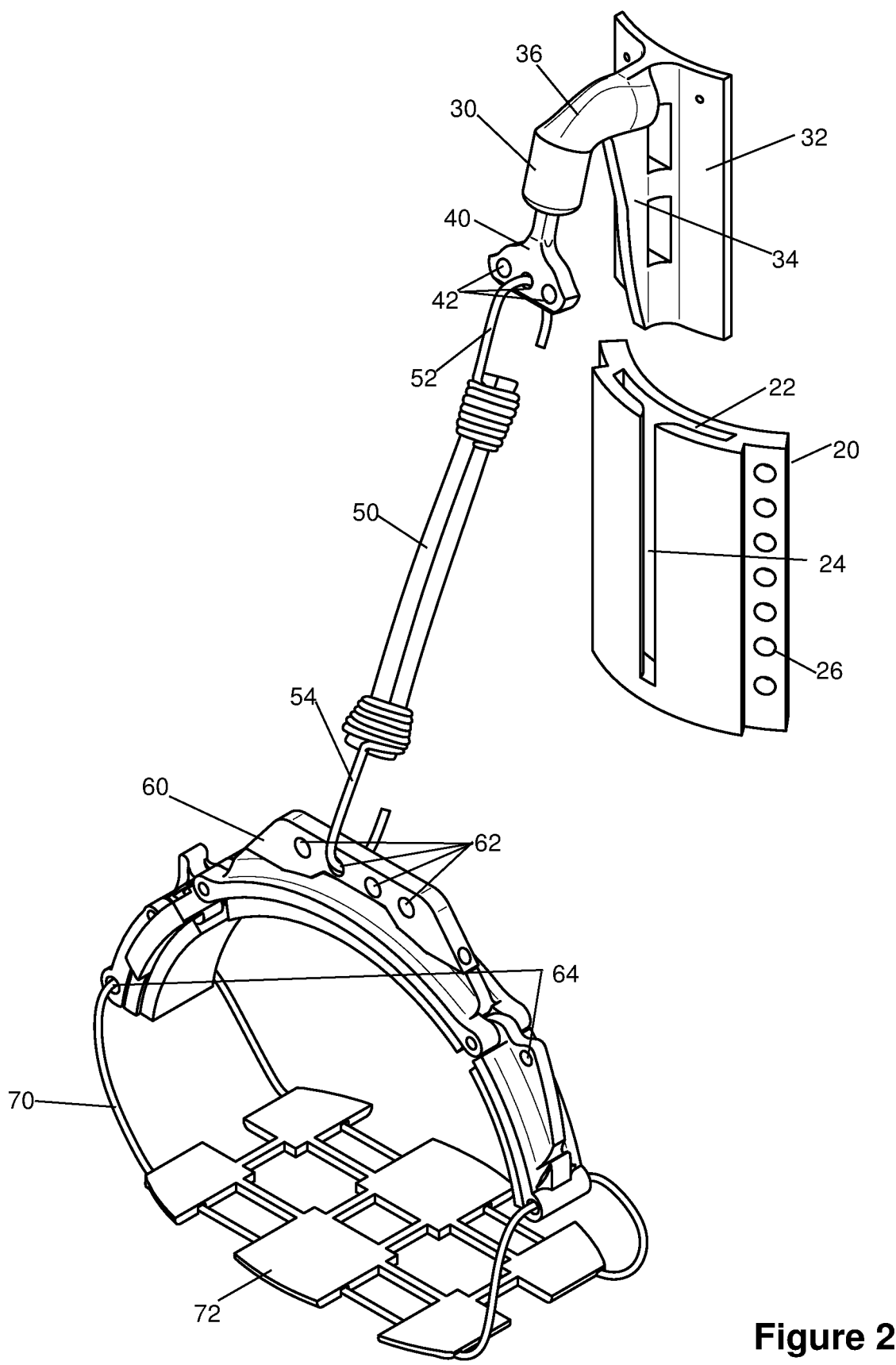
FIG. 2 shows a perspective view of the dorsiflexion assist device parts in an embodiment of the disclosed technology.
Figure 3:
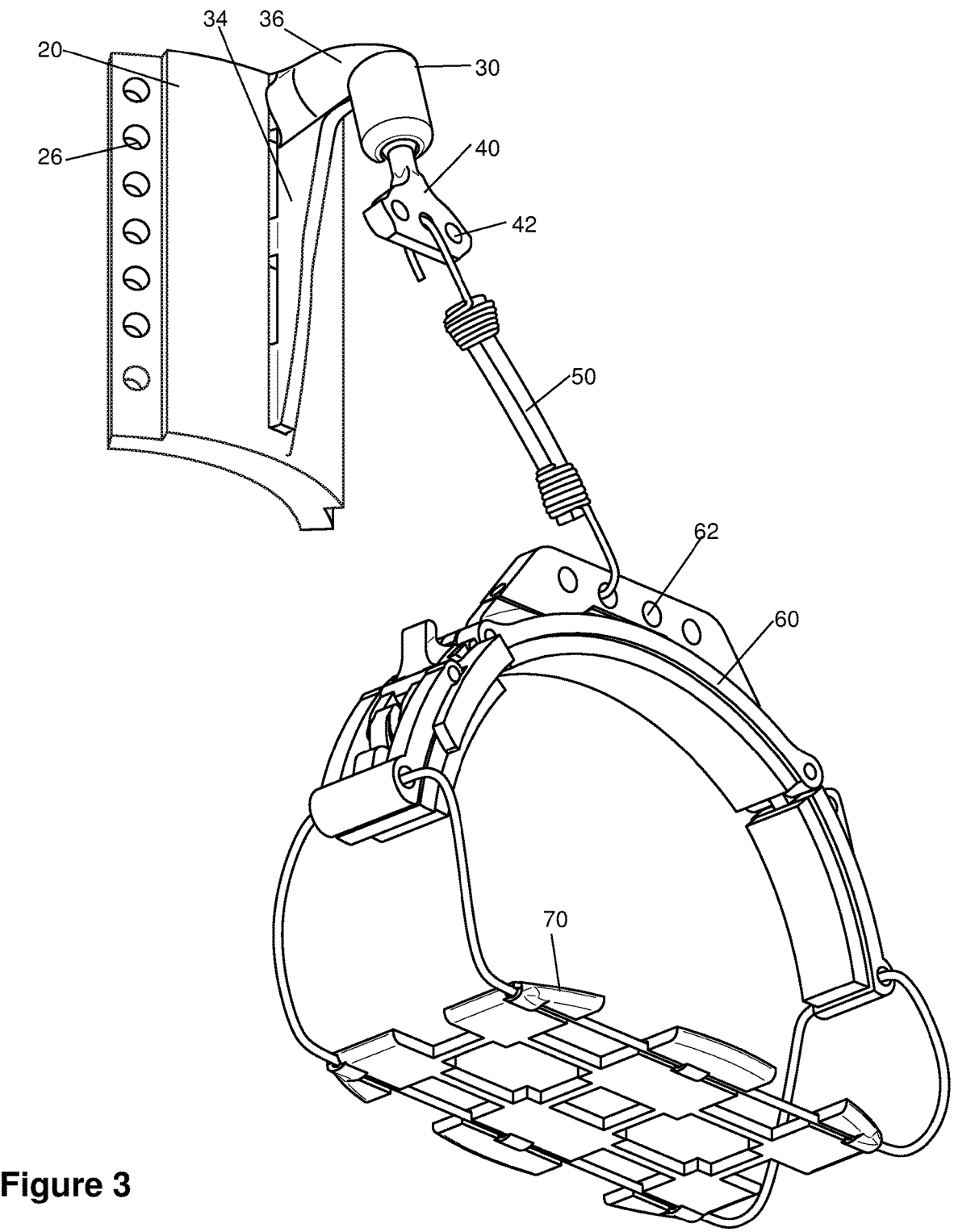
FIG. 3 shows bottom perspective view of the dorsiflexion assist device parts shown in FIG. 2.

FIG. 2 shows a perspective view of the dorsiflexion assist device parts in an embodiment of the disclosed technology. FIG. 3 shows bottom perspective view of the dorsiflexion assist device parts shown in FIG. 2. In these more detailed views, one can see that the anterior member 20 has an upward-facing (superior) portal or slot 22 joined with an anterior (front) portal 24 on a backplate with connecting portals 26, the connecting portals 26 allowing for attachment of a band there-to to hold the anterior member 20 against an ankle. The anterior member 20 is curved in an embodiment of the disclosed technology, to fit around the contour of an ankle.

The connecting flange 30 can have a backplate 32 having a width (lateral direction) equal to the width of the slot 22. The width of a forward-extending flange 34, which extends perpendicular to the backplate 32, is less than or equal to that of the anterior portal 24 of the anterior member 20. This allows the connecting flange 30 to be slid down through the superior portal 22 while the forward-extending flange 34 extends out of the anterior portal 24. The connecting flange 30 is then interchangeable with another should a different size anterior flange 30 be needed.

The multi-portal connecting end 40 has a plurality of portals 42 in embodiments of the disclosed technology. The tensioned cord 50 is removably connected by an end connector 52 there-in to one of the portals, such as a medial portal or a portal which is more lateral than another. Some wearers need dorsiflexion assist on a left or right side more than the other side, or pull more from a left to right side or vice versa. As such, one can attach the tensioned cord 50 by way of its end connectors 52 and 54 to one of a plurality of portals 42 or 62, accordingly. The portals 62 of the foot connector 60, likewise, can have a plurality of portals which are inline/parallel with one another, some of which are more medial or more lateral than others, some of which are more to the left or right than a medial line. Further, the foot connector 60 can have additional portals 64 which are more inferior than the portals 62 at the top side of the foot connector 60. Usage of such portals may be to aid with eversion. The tensioned cord 60 can be connected to one of these more interior and/or more lateral portals in embodiments of the disclosed technology. A bottom side of the foot connector 72 can be designed to fit within or be held against tread of the footwear 100 while sides 70 attach the bottom to the top end 60 to surround the article of footwear.

Figure 4:
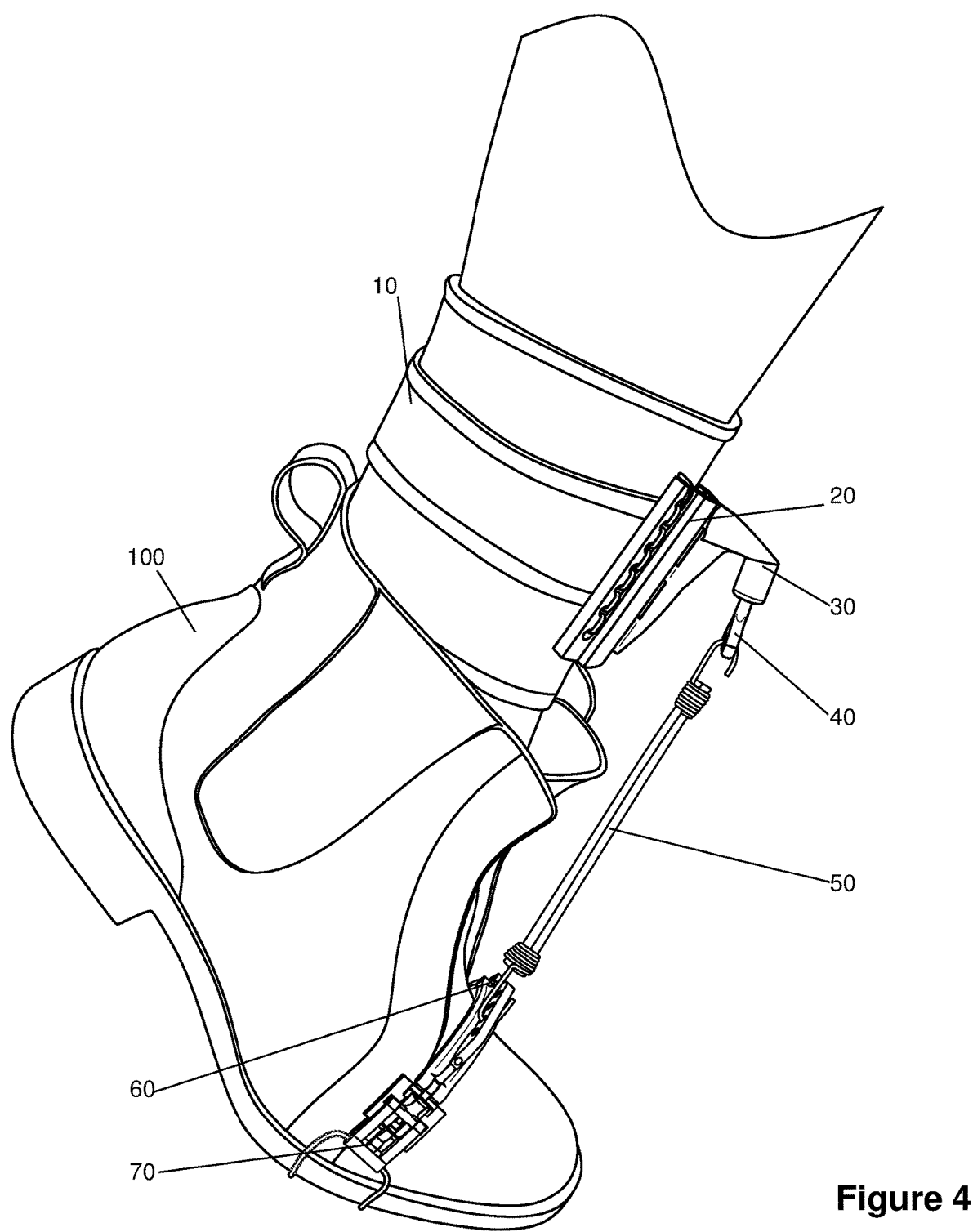
FIG. 4 shows the dorsiflexion assist device of the previous figures used assisting a wearer's step.

FIG. 4 shows the dorsiflexion assist device of the previous figures used assisting a wearer's step. Here, as the wearer of the dorsiflexion assist device lifts his heal off the ground, he/she is assisted with bringing his/her ankle towards his foot (dorsiflexing). The tensioned cord 50 applies force pulling the anterior side of the ankle towards the superior side of the foot aiding the flexation of the foot and ankle with respect to each other as shown. To accommodate the change in position of the ankle with respect to the foot, the angle of the tensioned cord 50 is changed while walking by way of the connecting end 40 moving towards/away from the ankle in a distal/proximal direction as the person takes his/her step. The movement and/or resting position of the connecting 40 in a medial/lateral direction is set by the angle of the tensioned cord 50 from the connecting 40 to the foot connector 60 in some embodiments of the disclosed technology.

Figure 5:
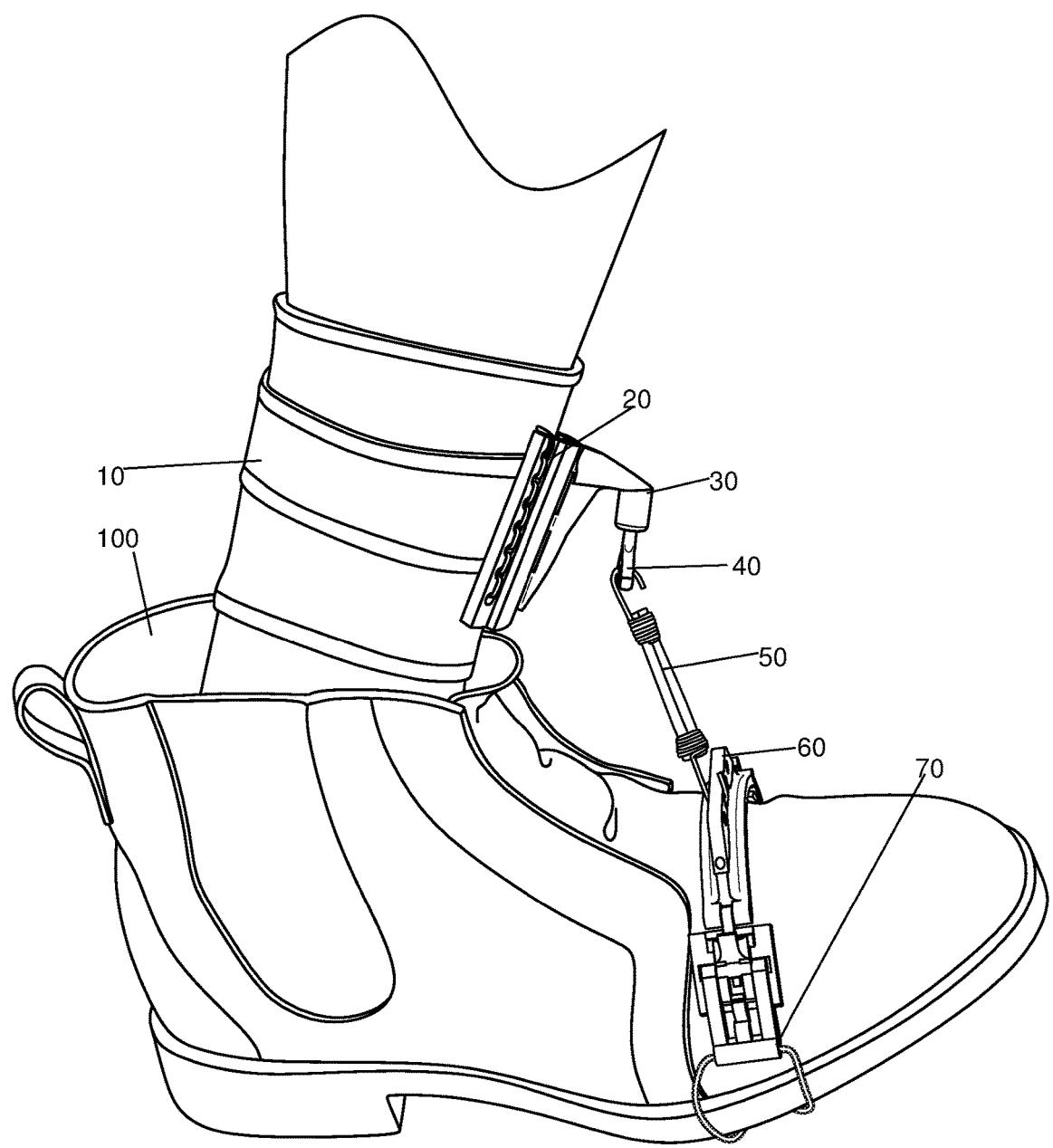
FIG. 5 shows the dorsiflexion assist device of FIG. 4 after a wearer completes a step.

FIG. 5 shows the dorsiflexion assist device of FIG. 4 after a wearer completes a step. As a person lands on their heal, their leg is pushed forward decreasing the distance from an anterior side of the ankle and superior side of the foot, releasing tension on the tensioned cord 50 such that the tensioned cord returns, in some embodiments, to it's resting length. Once the next step is taken and/or as the person straights (further uprights) their leg with respect to their foot, the tensioned cord 50 may be stretched again.

Figure 6:
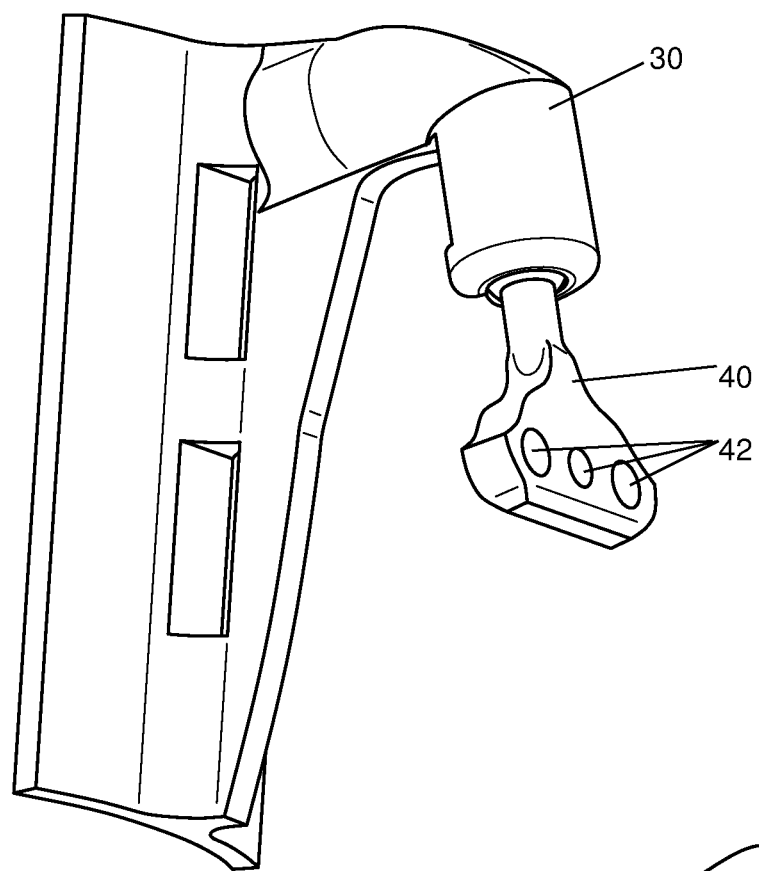
FIG. 6 shows a slidable member, connecting flange, and a multi-portal connecting end used in embodiments of the disclosed technology.
Figure 7:
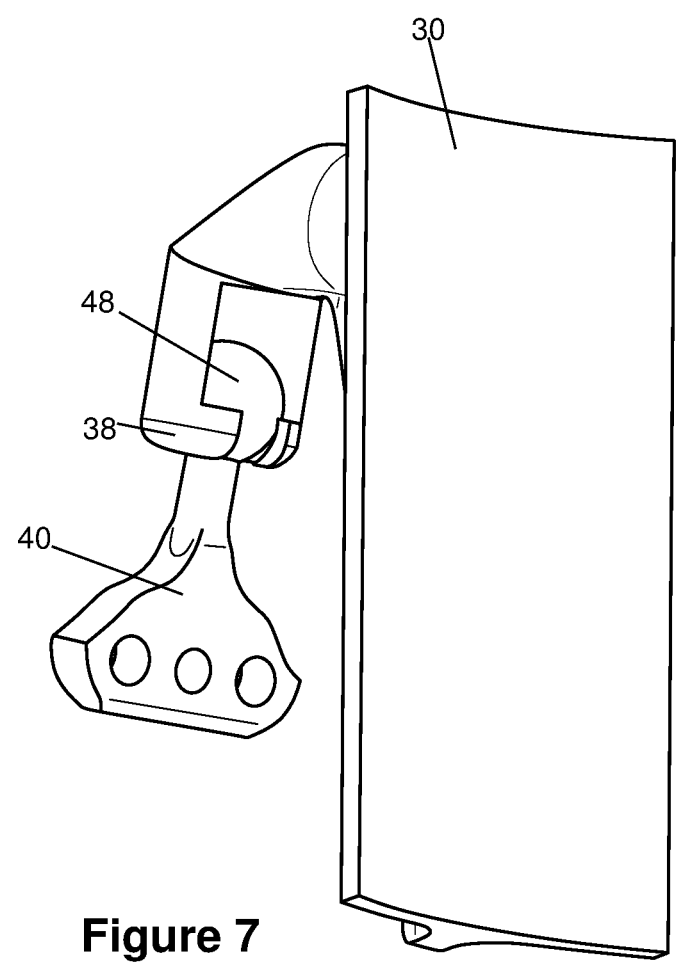
FIG. 7 shows a reverse side view of the slidable member, connecting flange, and multi-portal connecting end shown in FIG. 6.
Figure 8:
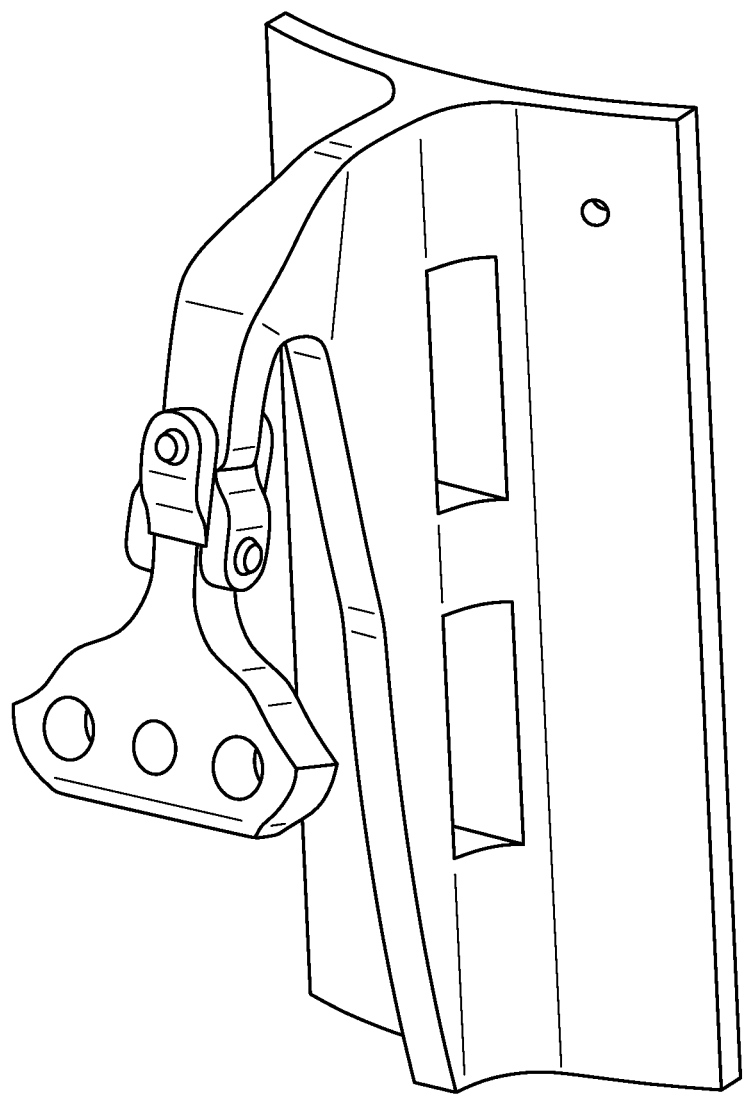
FIG. 8 shows another perspective view of the slidable member, connecting flange, and multi-portal connecting end of FIG. 6.

FIG. 6 shows a slidable member, connecting flange, and a multi-portal connecting end used in embodiments of the disclosed technology. FIG. 7 shows a reverse side view of the slidable member, connecting flange, and multi-portal connecting end shown in FIG. 6. FIG. 8 shows another perspective view of the slidable member, connecting flange, and multi-portal connecting end of FIG. 6. Note here that when seen from the back side, the bearing member 48 (spherical region connected to a post) is seen, held by flanges 38 around a lower side of the bearing member. Thus, the connecting 40 can be moved left/right, front/back, and combinations of these directions.

Figure 9:
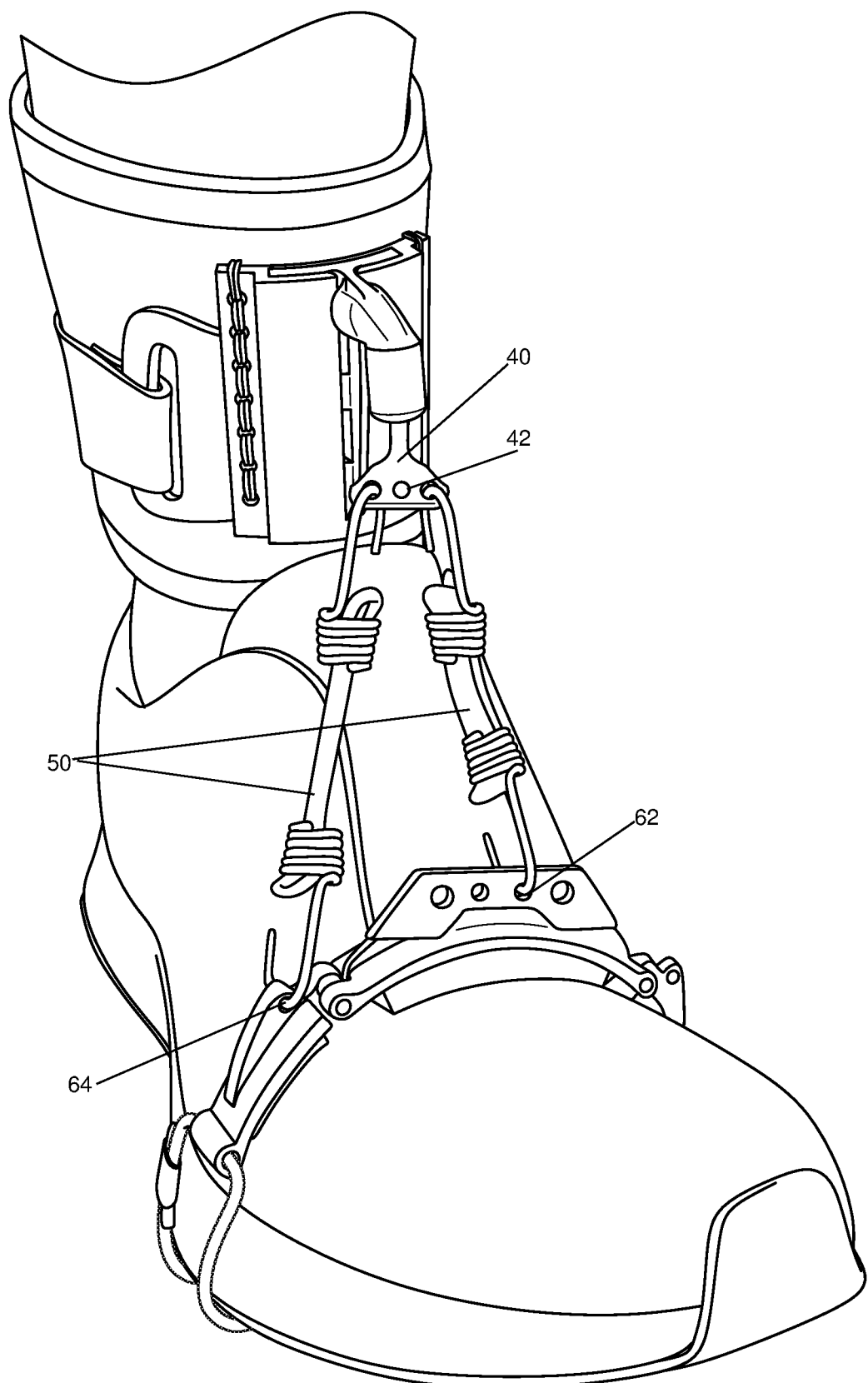
FIG. 9 shows an embodiment of the dorsiflexion assist device of the previous figures with multiple tensioned cords used.

FIG. 9 shows an embodiment of the dorsiflexion assist device of the previous figures with multiple tensioned cords used. In this embodiment, one tensioned cord 50 is placed on a left side and connects to a top-side connector 62 of the foot connector 40. Another tensioned cord 50 is connected between a right side of the connecting flange 30 and a lateral side and more posterior connector 64. This allows for more tension by way of the use of two cords instead of one as well as the ability to target help with dorsiflexion or eversion more on one side than another.

Figure 10:
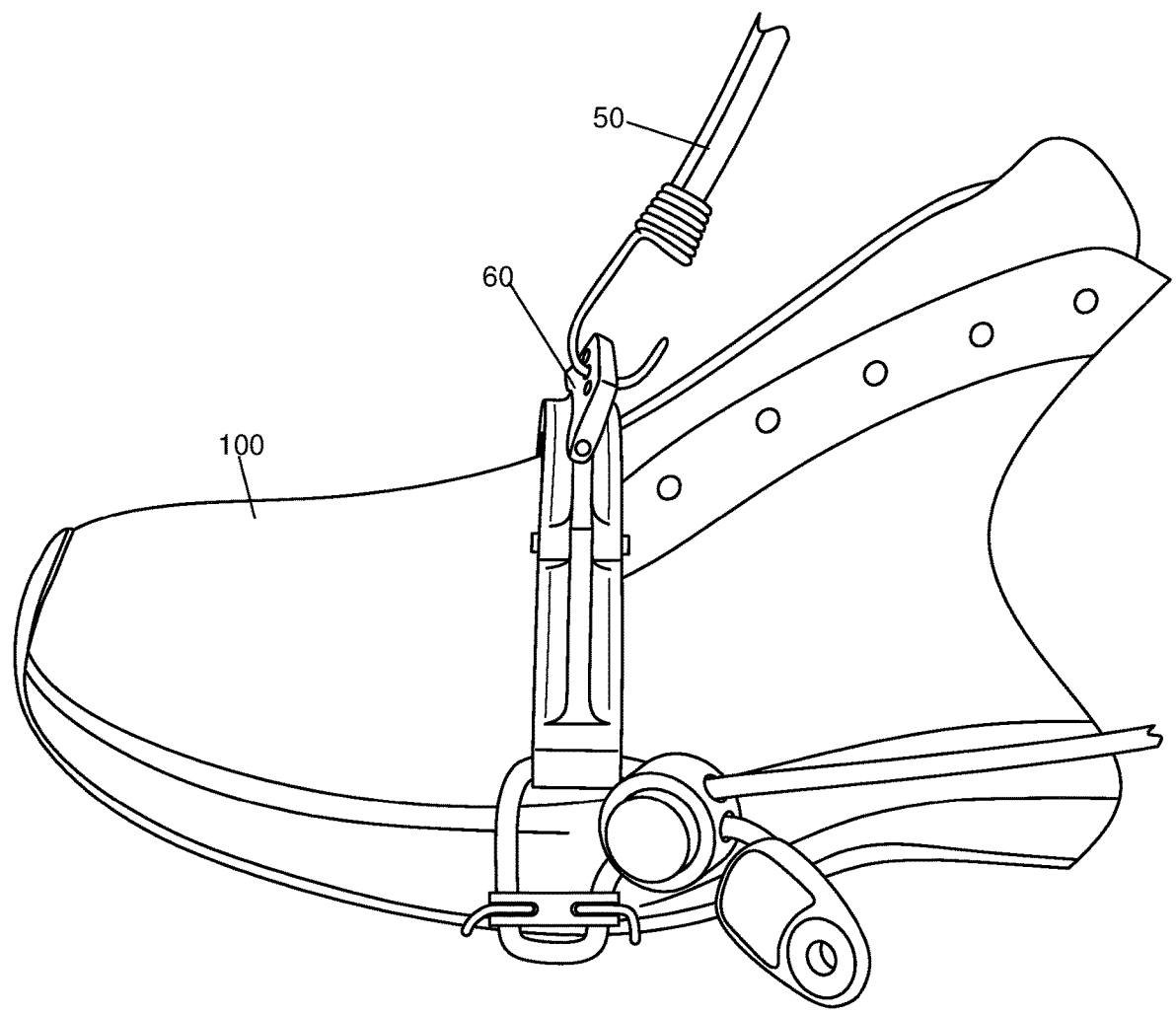
FIG. 10 shows a foot connector used with embodiments of the dorsiflexion assist device of the previous figures in an embodiment of the disclosed technology.
Figure 11:
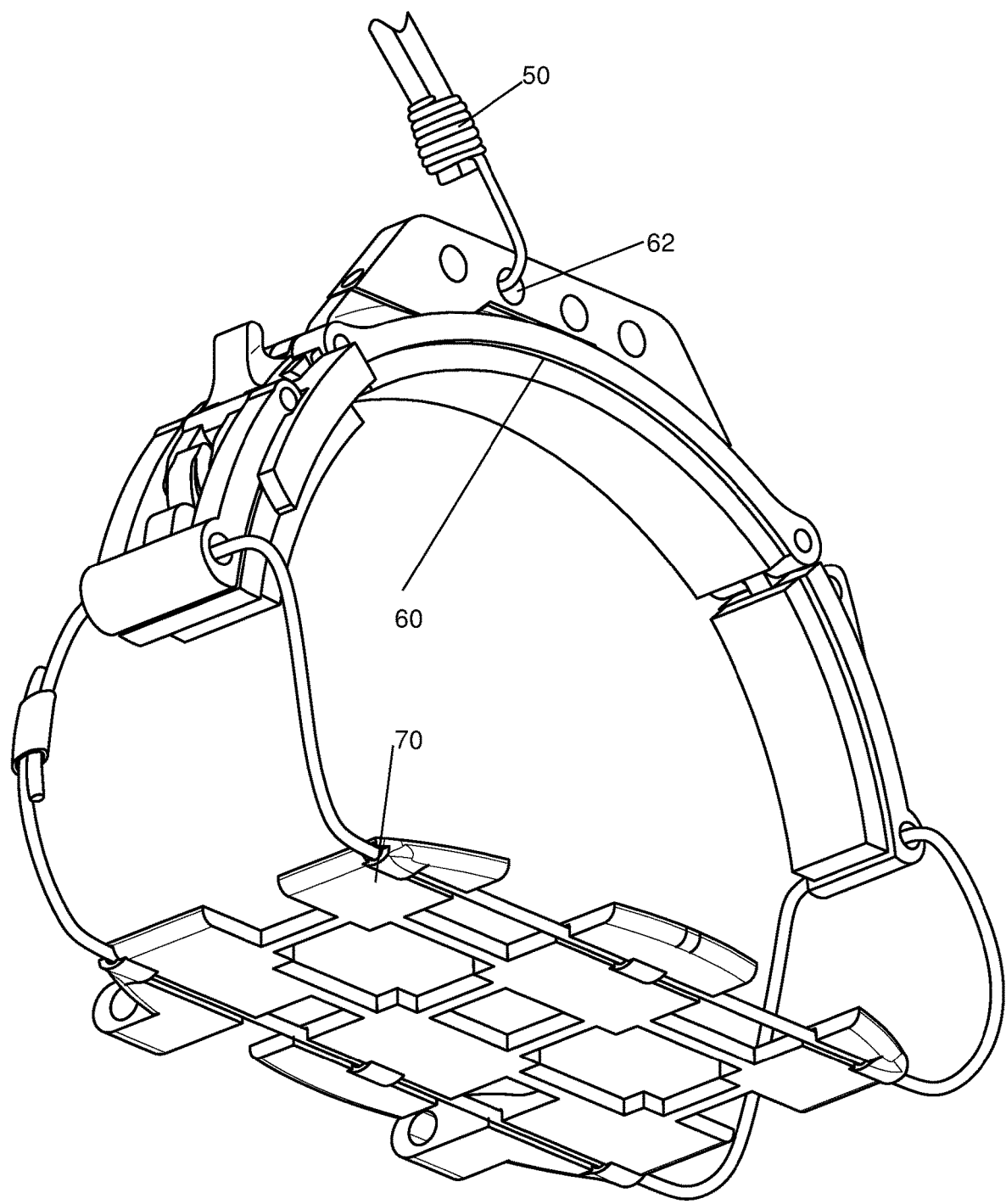
FIG. 11 shows a lower perspective view of the foot connector of FIG. 10.
Figure 12:
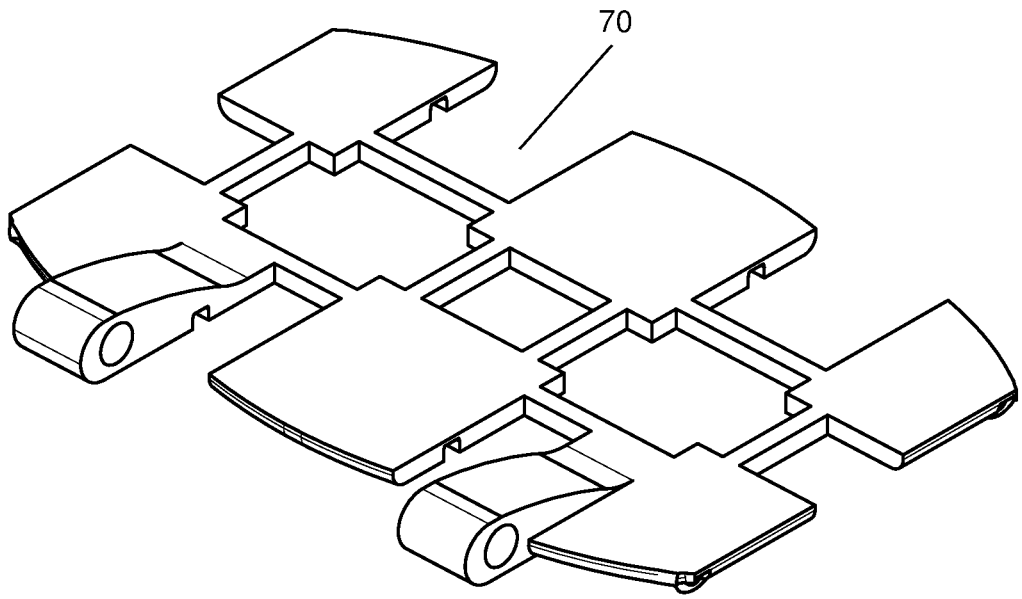
FIG. 12 shows a bottom piece of the foot connector of FIG. 10.
Figure 13:
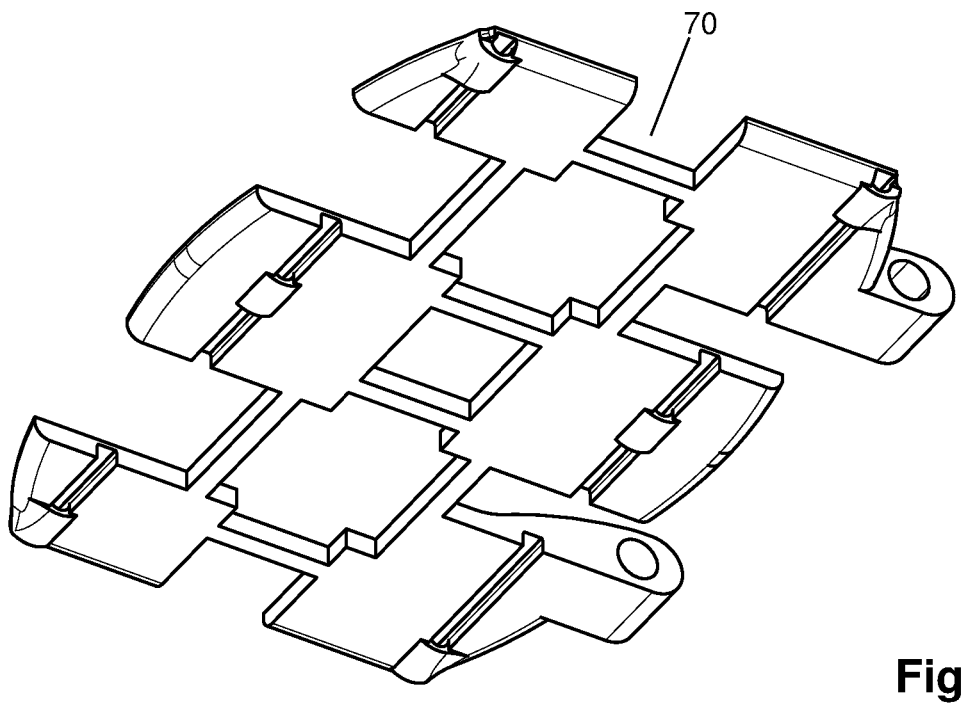
FIG. 13 shows a bottom side of the bottom piece of the foot connector of FIG. 10.

FIG. 10 shows a foot connector used with embodiments of the dorsiflexion assist device of the previous figures in an embodiment of the disclosed technology. FIG. 11 shows a lower perspective view of the foot connector of FIG. 10. FIG. 12 shows a bottom piece of the foot connector of FIG. 10. FIG. 13 shows a bottom side of the bottom piece of the foot connector of FIG. 10. These figures show further sides of the foot connector.

Figure 14:
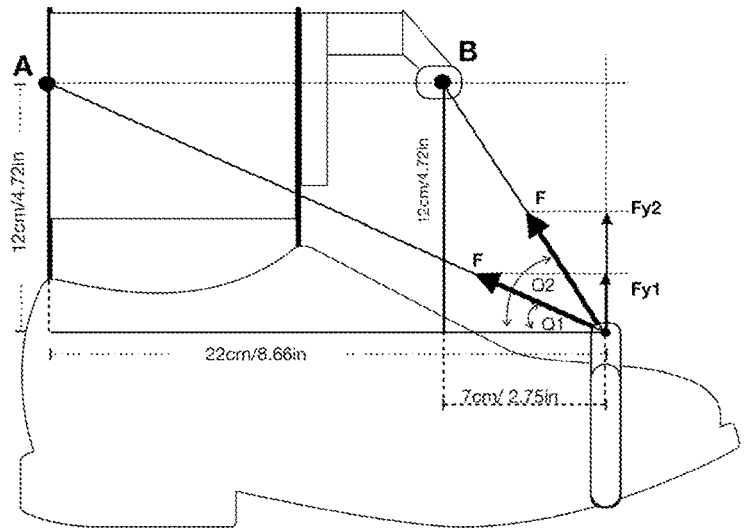
FIG. 14 shows the efficacy of the dorsiflexion assist device.

FIG. 14 shows the efficacy of the dorsiflexion assist device. An analysis of the use of force resolution and trigonometric angles is show demonstrating that the vertical force (Fy) is increased for dorsiflexion movement. "Setup-A" shows with no flange extension. "Setup-B" shows with connecting flange extension. An 80.5% greater force was found when adding a tension cord between points B and the top of the foot connector 70 than without.

For purposes of this disclosure, the term "substantially" is defined as "at least 95% of" the term which it modifies.

Any device or aspect of the technology can "comprise" or "consist of" the item it modifies, whether explicitly written as such or otherwise.

When the term "or" is used, it creates a group which has within either term being connected by the conjunction as well as both terms being connected by the conjunction.

While the disclosed technology has been disclosed with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described herein-above are also contemplated and within the scope of the invention.

The invention claimed is:

1. A dorsiflexion assist device which is adapted to extend around an ankle comprising:
    an anterior member with a substantially vertically disposed portal including a slot at a superior end thereof and an opening at an anterior end thereof, said slot having an interior which is wider in a lateral direction than said opening;
    a slidable member sized to fit across said lateral direction of said slot;
    a connecting flange extending through said opening of said substantially vertically disposed portal and fixed to said slidable member;
    a multi-portal connecting end connected to said connecting flange by a bearing allowing movement in each of an anterior/posterior, lateral, and combined directions thereof.

2. The dorsiflexion assist device of claim 1, further comprising a tensioned cord extending from a portal of said multi-portal connecting end to a foot connector, said tensioned cord attaching at a dorsal side of said foot connector.

3. The dorsiflexion assist device of claim 2, wherein said multi-portal connecting end comprises at least three substantially identical portals in parallel to one another, and a central portal of said at least three portals is inline with said connecting flange and centered with respect to said anterior member.

4. The dorsiflexion assist device of claim 3, wherein said foot connector comprises a plurality of portals in parallel to one another, each of said portals extending between an anterior side and a posterior side of said foot connector.

5. The dorsiflexion assist device of claim 4, wherein said tensioned cord is connected to said portal of said multi-portal connecting end and a portal of said foot connector based on a lateral location of each respective portal in order to assist a greater dorsiflexion of greater on a lateral side of a foot and/or ankle where assistance is most required.

6. The dorsiflexion assist device of claim 1, wherein said slidable member and said connecting flange are movable from said superior end to said anterior end within said anterior member, and said anterior member is adapted to be fixed relative to an ankle of a wearer thereof.

7. The dorsiflexion assist device of claim 6, wherein said multi-portal connecting end is simultaneously angularly and rotationally connected to said connecting flange and held in place relative to said anterior member when held taut, by way of a foot connector, to a dorsal side of a foot.

8. The dorsiflexion assist device of claim 7, wherein said foot connector extends around an article of footwear and dorsal muscles of the foot.

9. The dorsiflexion assist device of claim 8, wherein said foot connector comprises a plurality of first portals in parallel to each other and at least one additional portal which is more inferior and lateral in directional position to said plurality of first portals.

10. The dorsiflexion assist device of claim 9, further comprising two tensioned cords:
a first tensioned cord extending between a first portal of said multi-portal connecting end and one portal of said plurality of first portals of said foot connector; and
a second tensioned cord extending between a second portal of said multi-portal connecting end which is in parallel with said first portal of said multi-portal connecting end and said at least one additional portal of said foot connector.

11. A method of using a dorsiflexion assist device comprising the following steps, in any order:
securing an ankle connector in a fixed position around an ankle;
securing a foot connector in a fixed position around an anterior and dorsal end of a foot;
aligning an anterior connector of said ankle connector on an anterior side of said ankle;
sliding a slidable member through a superior end of a portal of said anterior connector causing a connecting flange to extend through an anterior portal of said ankle connector;
connecting a first end of a first tensioned cord to a portal of a multi-portal connector, said multi-portal connector rotatably held to said slidable member;
connecting a second end of said first tensioned cord to a portal fixed to said foot connector.

12. The method of claim 11, wherein a selection of said portal of said multi-portal connector selected based on a distance from a medial center of said ankle connector, said selection further based on a portion of dorsal muscles which are most in need of assistance with dorsiflexion.

13. The method of claim 12, wherein said connecting of said second end of said first tensioned cord is based on a selection of said portal from a plurality of portals of said foot connector due to a lateral/medial position thereof which is determined to be medically most beneficial for assistance with dorsiflexion.

14. The method of claim 11, further comprising a step of connecting an additional second tensioned cord between a second portal of said multi-portal connector and a second portal of said foot connector.

15. The method of claim 14, wherein said second portal of said foot connector is positioned in a more inferior and lateral position compared to said portal of said foot connector connected to said second end of said first tensioned cord.

16. The method of claim 12, wherein said connecting of said second end of said first tensioned cord is based on a selection of a portal of said portals of said foot connector due to a lateral/medial position thereof which is determined to be medically most beneficial for assistance with eversion.

* * * * *